(12) United States Patent
Jessen et al.

(10) Patent No.: US 6,228,992 B1
(45) Date of Patent: May 8, 2001

(54) PROTEINS FOR CONTROL OF NEMATODES IN PLANTS

(75) Inventors: Holly J. Jessen, Ankeny; Terry EuClaire Meyer, Urbandale, both of IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/412,102

(22) Filed: Oct. 4, 1999

Related U.S. Application Data

(62) Division of application No. 09/217,787, filed on Dec. 21, 1998.
(60) Provisional application No. 60/085,838, filed on May 18, 1998.

(51) Int. Cl.$^7$ .............................. C07K 1/00; C07K 14/00; C07K 16/00; C07K 17/00; A61K 35/78
(52) U.S. Cl. .................... 530/370; 530/376; 530/378; 530/379; 800/302; 800/312; 800/320.1
(58) Field of Search ..................................... 530/379, 350, 530/370, 372, 376, 378; 800/302, 312, 320.1

(56) References Cited

FOREIGN PATENT DOCUMENTS

| WO93/19181 | 9/1993 | (WO) | ............................ | C12N/15/29 |
| WO95/20669 | 8/1995 | (WO) | ............................ | C12N/15/82 |
| WO98/12335 | 3/1998 | (WO) | ............................ | C12N/15/82 |

OTHER PUBLICATIONS

Burrows et al, Pestic. Sci, vol. 52, pp. 176–183, 1998.*
Milligan et al, Plant Cell, vol. 10, pp. 1307–1319, 1998.*
CAI et al., "Positional Cloning of a Gene for Nematode Resistance in Sugar Beet," *Science*, Feb. 7, 1997, pp. 832–834, vol. 275, No. 5301, USA.

GeneBank Report, Accession No. U79733; CAI et al., "Positional Cloning of a Gene for Nematode Resistance in Sugar Beet," *Science*, Feb. 7, 1997, pp. 832–834, vol. 275, No. 5301, USA; CAI et al., Direct Submission, Submitted Nov. 26, 1996.

Rounsley, S.D. et al., Arabidopsis Thaliana Chromosome II BAC T28M21 Genomic Sequence, EMBL Sequence Data Library, May 20, 1997, XP002104923, Accession No. AF002109, Heidelberg, Germany.

Nahm, B.H. et all, Large–Scale Sequencing Analysis of ESTs from Rice Immature Seed, EMBL Sequence Data Library, Jan. 21, 1998, XP002104922, Accession No. AF002109, Heidelberg, Germany

* cited by examiner

*Primary Examiner*—Paula Hutzell
*Assistant Examiner*—Ashwin Mehta
(74) *Attorney, Agent, or Firm*—Alston & Bird LLP

(57) ABSTRACT

The present invention relates to isolated DNA sequences capable of conferring nematode resistance in plants. The isolated DNA sequences can be inserted into a DNA vector to form a transformation construct for the expression of the isolated DNA sequences in plants. The transformation construct can be introduced into plant cells. Plants expressing the isolated DNA sequences can be regenerated from the transformed cells. Methods for improving genetic traits for nematode resistance in plants are also provided, comprising transforming cells with the isolated DNA sequences and regenerating plants from the transformed cells expressing the isolated DNA sequences necessary for nematode resistance.

4 Claims, 1 Drawing Sheet

PROTEINS FOR CONTROL OF NEMATODES IN PLANTS

CROSS-REFERENCE TO RELATED APPLICATION

This application claims the benefit of U.S. Provisional Application Serial No. 60/085,838, filed May 18, 1998 and is a Divisional U.S. application of application Ser. No. 09/217,787 (pending), filed Dec. 21, 1998.

FIELD OF THE INVENTION

The present invention relates to isolated DNA sequences involved in nematode resistance in lants. The invention also relates to methods for improving the genetic traits for nematode resistance in plants by utilizing such isolated DNA sequences.

BACKGROUND

Plants are continually attacked by a diverse range of phytopathogenic organisms. These organisms cause substantial losses to crops each year. Traditional approaches for control of plant diseases have been the use of chemical treatment and the construction of interspecific hybrids between resistant crops and their wild-type relatives as sources of resistant germplasm. However, environmental and economic concerns make chemical pesticides undesirable, while the traditional interspecific breeding is inefficient and often cannot eliminate the undesired traits of the wild species. Thus, the discovery of pest and pathogen-resistant genes provides a new approach to control plant disease.

Several genes responsible for disease resistance have been identified and isolated from plants. See Staskawicz et al. (1995) *Science* 268:661–667. Recently, the sugar beet Hs1$^{pro-1}$ gene that confers resistance to the beet cyst nematode was cloned. See Cai et al. (1997) *Science* 275:832–834; and Moffat (1997) *Science* 275:757. Transformation of plants or plant tissues with the resistance genes can confer disease resistance to susceptible strains. See, for example, PCT Publication WO93/19181; and Cai et al. (1997) *Science* 275:832–834.

Nematode infection is prevalent in many crops. For example, soybean cyst nematode (*Heterodera glycines*) is a widespread pest that causes substantial damage to soybeans every year. Such damage is the result of the stunting of the soybean plant caused by the cyst nematode. The stunted plants have smaller root systems, show symptoms of mineral deficiencies in their leaves, and wilt easily. The soybean cyst nematode is believed to be responsible for yield losses in soybeans that are estimated to be in excess of $500 million per year.

Nematicides such as Aldicarb and its breakdown products are known to be highly toxic to mammals. As a result, government restrictions have been imposed on the use of these chemicals. Thus, there is a great need for the isolation of genes that can provide an effective method of controlling nematodes without causing health and environmental problems.

SUMMARY OF THE INVENTION

This invention relates to DNA sequences isolated from soybean and maize. The sequences alone, or in combination with other sequences, confer nematode resistance in a plant. The sequences are useful in methods for the protection of plants from nematodes. Additionally, allelic variants of the resistance gene from a susceptible plant are included. In another aspect of the present invention, expression cassettes and transformation vectors comprising the isolated nucleotide sequences are disclosed. The transformation vectors can be used to transform plants and express the nematode resistance genes in the transformed cells. Plants susceptible to nematode infection can be targeted to confer nematode resistance. The transformed cells as well as the regenerated transgenic plants containing and expressing the isolated DNA and protein sequences are also disclosed.

DETAILED DESCRIPTION OF THE INVENTION

Figure 1:
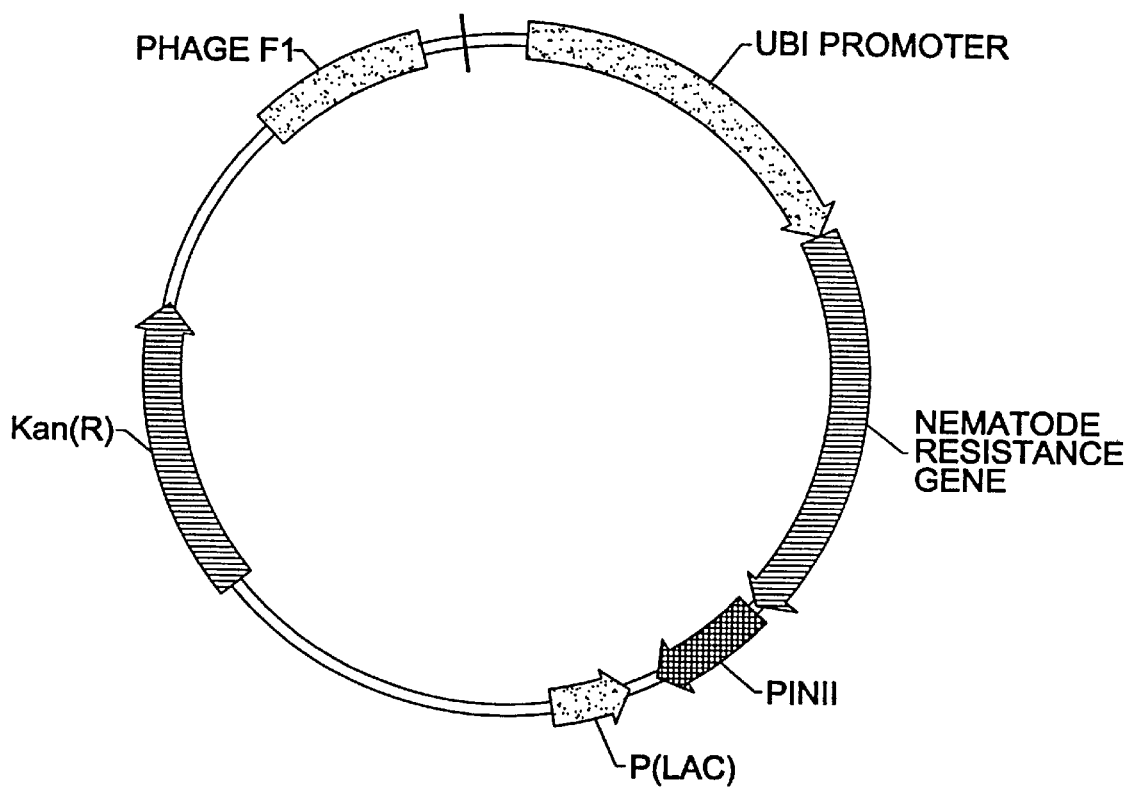
FIG. 1 schematically illustrates the plasmid vector comprising a nematode resistance DNA sequence of the present invention operably linked to the ubiquitin promoter. Constitutive expression of this sequence confers resistance to nematodes in a transformed plant.

Compositions and methods for the control of nematodes in susceptible plants are provided. The compositions comprise isolated proteins and DNA sequences encoding such proteins involved in nematode resistance. Such isolated DNA sequences can be transferred into plants to confer or improve nematode resistance in the transformed plants. Sequences of the invention have been isolated from maize and soybean. By "involved in nematode resistance" is intended that the proteins or sequences, either alone or in combination with other proteins or sequences, confer nematode resistance in a plant. In this manner, resistance to nematodes can be enhanced or improved in the transformed plant as at least one of the sequences required for nematode resistance is provided.

DNA sequences isolated from the genomes of maize and soybean are disclosed. The nucleotide sequences and amino acid sequences from two maize isolates are set forth in SEQ ID NOs: 1–2 and 3–4, and the corresponding sequences from two soybean isolates are set forth in SEQ ID NOs: 5–6 and 7–8. The nucleotide sequences in accordance with this invention are involved in nematode resistance in plants and may confer, alone or in combination with other sequences, nematode resistance in plants. Also discussed are DNA sequences isolated from a susceptible genotype of soybean. The nucleotide and amino acid sequences for this isolate are set forth in SEQ ID NOs: 9–10. Nucleotide sequences of the invention also include the maize and soybean nematode resistance gene sequences as contained in plasmids deposited with American Type Culture Collection (ATCC) and assigned Accession Numbers 209366, 209365, 209614, 209363, and 209364.

Using the sequence information set forth in the SEQ ID NOs or the sequences as contained in ATTC deposits assigned Accession Nos. 209366, 209365, 209614, 209363, and 209364, other plant DNA sequences comprising the nucleotide sequences disclosed above can be isolated based on sequence homology at either the amino acid or nucleotide sequence level. Any suitable molecular cloning method can be used including, but not limited to, PCR amplification and DNA hybridization. In the same manner, synthetic nucleotide sequences can be designed based on the amino acid sequences of the invention. Methods to design and make such synthetic sequences are available in the art.

In a hybridization method, the hybridization probes may be genomic DNA fragments, cDNA fragments, RNA fragments, or other oligonucleotides, and may be labeled with a detectable group such as $^{32}$P, or any other detectable marker. Probes for hybridization can be made by labeling synthetic oligonucleotides based on the sequence of the soybean and/or maize sequence. Degenerate primers designed on the basis of conserved nucleotide or amino acid sequences in the maize and soybean sequences can additionally be used. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), hereby incorporated by reference. The labeled probes can be used to screen cDNA or genomic libraries made from nematode resistant plants. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

In a PCR method, the DNA or amino acid sequence encoded by the soybean or maize sequences of the invention can be aligned with each other. Nucleotide primers can be designed based on any conserved short stretches of amino acid sequences or nucleotide sequences. Pairs of primers can be used in PCR reactions for amplification of DNA sequences from cDNA or genomic DNA extracted from plants of interest. In addition, a single specific primer with a sequence corresponding to one of the nucleotide sequences disclosed herein can be paired with a primer having a sequence of the DNA vector in the cDNA or genomic libraries for PCR amplification of the sequences 5' or 3' to the nucleotide sequences disclosed herein. Similarly, nested primers may be used instead of a single specific primer for the purposes of the invention. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.).

The sequences of the invention comprise coding sequences from other plants that may be isolated according to well-known techniques based on their sequence homology to the maize or soybean coding sequences set forth herein. In these techniques, all or part of the known coding sequence is used as a probe that selectively hybridizes to other possible nematode resistance coding sequences present in a population of cloned genomic DNA fragments or cDNA fragments (i.e., genomic or cDNA libraries) from a chosen organism. To achieve specific hybridization under a variety of conditions, such probes include sequences that are unique and are preferably at least about 10 nucleotides in length, and most preferably at least about 20 nucleotides in length. Such probes may be used to amplify corresponding coding sequences from a chosen organism by PCR. This technique may be used to isolate other possible nematode resistance coding sequences from a desired organism or as a diagnostic assay to determine the presence of the nematode resistance coding sequence in an organism.

Such techniques include hybridization screening of plated DNA libraries (either plaques or colonies; see, e.g., Innis et al., eds. (1990) *PCR Protocols: A Guide to Methods and Applications* (Academic Press, New York)).

The isolated DNA sequences further comprise DNA sequences isolated from other plants by hybridization with partial sequences obtained from maize and soybean. Conditions that will permit other DNA sequences to hybridize to the DNA sequences disclosed herein can be determined in accordance with techniques generally known in the art. For example, hybridization of such sequences may be carried out under conditions of reduced stringency, medium stringency, or high stringency conditions (e.g., conditions represented by a wash stringency of 35–40% Formamide with 5×Denhardt's solution, 0.5% SDS, and 1×SSPE at 37° C.; conditions represented by a wash stringency of 40–45% Formamide with 5×Denhardt's solution, 0.5% SDS, and 1×SSPE at 42° C.; and conditions represented by a wash stringency of 50% Formamide with 5×Denhardt's solution, 0.5% SDS, and 1×SSPE at 42° C., respectively. See Sambrook et al. (1989) *Molecular Cloning: A Laboratory Manual* (2d ed., Cold Spring Harbor Laboratory Press, Plainview, N.Y.). In general, sequences that confer nematode resistance and hybridize to the DNA sequences disclosed herein will be at least 70–75% homologous, 80–85% homologous, and even 90–95% homologous or more.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset of or the entire specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or more contiguous nucleotides in length. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Optimal alignment of sequences for comparison may be conducted by the local homology algorithm of Smith and Waterman (1981) *Adv. Appl. Math.* 2:482; by the homology alignment algorithm of Needleman and Wunsch (1970) *J. Mol. Biol.* 48:443; by the search for similarity method of Pearson and Lipman (1988) *Proc. Natl. Acad. Sci.* 85:2444; by computerized implementations of these algorithms, including, but not limited to: CLUSTAL in the PC/Gene program by Intelligenetics (Mountain View, Calif.), GAP, BESTFIT, BLAST, FASTA, and TFASTA in the Wisconsin Genetics Software Package, Genetics Computer Group (GCG) (575 Science Drive, Madison, Wis.); the CLUSTAL program is well described by Higgins and Sharp (1988) *Gene* 73:237–244; Higgins and Sharp (1989); *CABIOS* 5:151–153; Corpet et al. (1988) *Nucleic Acids Res.* 16:10881–90; Huang et al. (1992) *Computer Applications in the Biosciences* 8:155–65; and Person et al. (1994) *Meth. of Mol. Biol.* 24:307–331; preferred computer alignment methods also include the BLASTP, BLASTN, and BLASTX algorithms. See Altschul et al. (1990) *J. Mol. Biol.* 215:403–410. Alignment is also often performed by visual inspection and manual alignment.

(c) As used herein, "sequence identity" or "identity" in the context of two nucleic acid or polypeptide sequences includes reference to the residues in the two sequences that are the same when aligned for maximum correspondence over a specified comparison window. When percentage of sequence identity is used in reference to proteins, it is recognized that residue positions that are not identical often differ by conservative amino acid substitutions, where amino acid residues are substituted for other amino acid residues with similar chemical properties (e.g., charge or hydrophobicity) and therefore do not substantially change the functional properties of the molecule. Where sequences differ in conservative substitutions, the percentage of sequence identity may be adjusted upward to correct for the conservative nature of the substitution. Sequences that differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage of sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent temperature conditions are selected to be about 5° C. to about 2° C. lower than the melting point ($T_m$) for the specific sequence at a defined ionic strength and pH. The denaturation or melting of DNA occurs over a narrow temperature range and represents the disruption of the double helix into its complementary single strands. The process usually is characterized by the temperature of the midpoint of transition, $T_m$, which is sometimes described as the melting temperature. Formulas are available in the art for the determination of melting temperatures. Typically, stringent wash conditions are those in which the salt concentration is about 0.02 molar at pH 7 and the temperature is at 50, 55, or 60° C. However, nucleic acids that do not hybridize to each other under stringent conditions are still substantially identical if the polypeptides that they encode are substantially identical. This may occur, for example, when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

(e) (ii) The terms "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Polypeptides that are "substantially similar" share sequences as noted above except that residue positions that are not identical may differ by conservative amino acid changes.

The present invention also encompasses the proteins and peptides encoded by the nucleotide sequences of this invention. It is recognized that the proteins of the invention may be oligomeric and will vary in molecular weight, component peptides, activity, and in other characteristics. The proteins of the invention can be used to protect plants against nematodes. Such methods are described in more detail below.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence confer resistance to nematodes. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the entire nucleotide sequence encoding the proteins of the invention.

By "variants" is intended substantially similar sequences. For nucleotide sequences, conservative variants include those sequences that, because of the degeneracy of the genetic code, encode the amino acid sequence of one of the proteins conferring resistance to nematodes. Generally, nucleotide sequence variants of the invention will have at least 70%, generally, 80%, preferably up to 90% sequence identity to its respective native nucleotide sequence.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulation are generally known in the art.

Thus, the proteins of the invention may be altered in various ways including amino acid substitutions, deletions, truncations, and insertions. Methods for such manipulations are generally known in the art. For example, amino acid sequence variants of the proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology*(MacMillan Publishing Company, New York) and the references cited therein. Thus, the genes and nucleotide sequences of the invention include both the naturally occurring sequences as well as mutant forms. Likewise, the proteins of the invention encompass both naturally occurring proteins as well as variations, fragments, and modified forms thereof. Such variants will continue to possess the desired activity of conferring resistance to nematodes. Obviously, the mutations that will be made in the DNA encoding the variant must not place the sequence out of reading frame and preferably will not create sequences deleterious to expression of the gene product. See, EP Patent Application Publication No. 75,444.

The nematode resistance genes of the invention can be optimized for enhanced expression in plants of interest. See, for example, EPA0359472; EPA0385962; WO91/16432; Perlak et al. (1991) *Proc. Natl. Acad. Sci. USA* 88:3324–3328; and Murray et al. (1989) *Nucleic Acids Res.* 17:477–498. In this manner, the genes can be synthesized utilizing plant-preferred codons. See, for example, Murray et al. (1989) *Nucleic Acids Res.* 17:477–498, the disclosure of which is incorporated herein by reference. In this manner, synthetic genes can also be made based on the distribution of codons a particular host uses for a particular amino acid. Thus, the nucleotide sequences can be optimized for expression in any plant. It is recognized that all or any part of the gene sequence may be optimized or synthetic. That is, synthetic or partially optimized sequences may also be used.

The present invention also relates to a recombinant DNA transformation construct comprising the isolated DNA sequences involved in nematode resistance in plants. The recombinant DNA transformation construct can be introduced into plant cells, protoplasts, calli, tissues, or whole plants to confer nematode-resistance properties in plants.

The sequences of the invention can be constructed in expression cassettes for expression in a plant. Such expression cassettes will comprise a transcriptional initiation region linked to the gene encoding the gene of interest. Such an expression cassette is provided with a plurality of restriction sites for insertion of the gene of interest behind the regulatory control of a designated promoter. The expression cassette may additionally contain selectable marker genes suitable for the particular host organism.

The transcriptional initiation region, the promoter, may be native or analogous or foreign or heterologous to the host. Additionally, the promoter may be the natural sequence or alternatively a synthetic sequence. By foreign is intended that the transcriptional initiation region is not found in the wild-type host into which the transcriptional initiation region is introduced. As used herein a chimeric gene comprises a coding sequence operably linked to a transcription initiation region which is heterologous to the coding sequence. While any promoter or promoter element capable of driving expression of a coding sequence can be utilized, of particular interest for expression in plants are root promoters (Bevan et al. (1993) in *Gene Conservation and Exploitation: Proceedings of the 20th Stadler Genetics Symposium*, ed. Gustafson et al. (Plenum Press, New York) pp. 109–129; Brears et al. (1991) *Plant J.* 1:235–244; Lorenz et al. (1993) *Plant J.* 4:545–554; U.S. Pat. Nos. 5,459,252; 5,608,149; 5,599,670); pith promoter (U.S. Pat. Nos. 5,466,785; 5,451,514; 5,391,725); or other tissue specific and constitutive promoters (see, for example, U.S. Pat. Nos. 5,608,149; 5,608,144; 5,604,121; 5,569,597; 5,466, 785; 5,399,680; 5,268,463; 5,608,142), herein incorporated by reference.

The transcriptional cassette will include in the 5'-to-3' direction of transcription, transcriptional and translational initiation regions, a DNA sequence of interest, and transcriptional and translational termination regions functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; Joshi et al. (1987) *Nucleic Acid Res.* 15:9627–9639.

Methodologies for the construction of plant transformation constructs are described in the art. The construct may include any necessary regulatory elements such as promoters, terminators (Guerineau et al. (1991) *Mol. Gen. Genet.* 226:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; Joshi et al. (1987) *Nucleic Acid Res.* 15:9627–9639); plant translational consensus sequences (Joshi, C. P. (1987) *Nucleic Acids Research* 15:6643–6653), enhancers, introns (Luehrsen and Walbot (1991) *Mol. Gen. Genet.* 225:81–93) and the like, operably linked to the nucleotide sequence. It may be beneficial to include 5' leader sequences in the transformation construct. Such leader sequences can act to enhance translation. See, for example, Elroy-Stein et al. (1989) *PNAS USA* 86:6126–6130; Allison et al. (1986); Macejak and Sarnow (1991) *Nature* 353:90–94; Jobling and Gehrke (1987) *Nature* 325:622–625; Gallie et al. (1989) *Molecular Biology of RNA*, pp. 237–256; Lommel et al. (1991) *Virology* 81:382–385; and Della-Cioppa et al. (1987) *Plant Physiol.* 84:965–968.

Transcriptional and translational regulatory signals include but are not limited to promoters, transcriptional initiation start sites, operators, activators, enhancers, other regulatory elements, ribosomal binding sites, an initiation codon, termination signals, and the like. See, for example, U.S. Pat. No. 5,039,523; U.S. Pat. No. 4,853,331; EPO 0480762A2; Sambrook et al. (1989) *Molecular Cloning: A Laboratory Manual* (2d ed., Cold Spring Harbor Laboratory Press, Plainview, N.Y.); Davis et al., eds. (1980) *Advanced Bacterial Genetics* (2d ed., Cold Spring Harbor Laboratory, Cold Spring Harbor, N.Y.); and the references cited therein.

For the expression of the proteins encoded by the isolated DNA sequences of the present invention, a promoter capable of facilitating gene transcription in plant cells must be operably linked to the nematode resistance gene sequence. A variety of suitable promoters are generally known in the art. Both constitutive promoter and tissue-specific promoters can be used. A constitutive promoter is a promoter that can initiate RNA transcription in any tissue or cell in a plant, while tissue-specific promoters can do so only in specific tissues. Suitable promoters are known in the art and include 35S and 19S promoter of CaMV, Agrobacterium NOS (nopaline synthase) gene promoter, and the *Agrobacterium mannopine* synthase gene promoter. For tissue specific expression, the isolated DNA sequences of the invention conferring nematode resistance can be operably linked to tissue specific promoters.

In addition, a marker gene for identifying and selecting transformed cells, tissues, or plants may be included in the transformation construct. By marker gene is intended to be either reporter genes or selectable marker genes.

Reporter genes are generally known in the art. The reporter gene used should be exogenous and not expressed endogenously. Ideally the reporter gene will exhibit low background activity and should not interfere with plant biochemical and physiological activities. The products expressed by the reporter gene should be stable and readily detectable. It is important that the reporter gene expression should be able to be assayed by a non-destructive, quantitative, sensitive, easy to perform and inexpensive method.

Examples of suitable reporter genes known in the art can be found in, for example, Jefferson et al. (1991) in *Plant Molecular Biology Manual*, ed. Gelvin et al. (Kluwer Academic Publishers), pp. 1–33; (DeWet et al. (1987) *Mol. Cell. Biol.* 7:725–737; Goffet al. (1990) *EMBO J.* 9:2517–2522; Kain et al. (1995) *BioTechniques* 19:650–655; Chiu et al. (1996) *Current Biology* 6:325–330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987–992; methotrexate (Herrera Estrella et al. (1983) *Nature* 303:209–213; Meijer et al. (1991) *Plant Mol. Biol.* 16:807–820); hygromycin Waldron et al. (1985) *Plant Mol. Biol.* 5:103–108; Zhijian et al. (1995) *Plant Science* 108:219–227); streptomycin (Jones et al. (1987) *Mol. Gen. Genet.* 210:86–91; spectinomycin (Bretagne-Sagnard et al. (1996) *Transgenic Res.* 5:131–137); bleomycin (Hille et al. (1990) *Plant Mol. Biol.* 7:171–176); sulfonamide (Guerineau et al. (1990) *Plant Mol. Biol.* 15:127–136); bromoxynil (Stalker et al .(1988) *Science* 242:419–423); glyphosate (Shaw et al. (1986) *Science* 233:478–481); phosphinothricin (DeBlock et al. (1987) *EMBO J.* 6:2513–2518); kanomycin, and the like.

It is further recognized that the components of the transformation construct may be modified to increase expression. For example, truncated sequences, nucleotide substitutions or other modifications may be employed. See, for example, Perlak et al. (1991) *Proc. Natl. Acad. Sci. USA* 88:3324–3328; Murray et al. (1989) *Nucleic Acids Res.* 17:477–498; and WO91/16432.

In preparing the transformation construct, the various DNA fragments may be manipulated, so as to provide for the DNA sequences in the proper orientation and, as appropriate in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, PCR, or the like may be employed, where insertions, deletions, or substitutions, e.g., transitions and transversions, may be involved.

The present invention also relates to the introduction of the transformation constructs into plant protoplasts, calli, tissues, or organ explants and the regeneration of transformed plants expressing the nematode resistance gene. The compositions of the present invention can be used to transform any plant. In this manner, genetically modified plants, plant cells, plant tissue, seed, and the like can be obtained. Transformation protocols may vary depending on the type of plant or plant cell, i.e., monocot or dicot, targeted for transformation. Suitable methods of transforming plant cells include microinjection (Crossway et al. (1986) *Biotechniques* 7:320–334), electroporation (Riggs et al. (1986) *Proc. Natl. Acad. Sci. USA* 83:5602–5606); Agrobacterium-mediated transformation (Hinchee et al. (1988) *Biotechnology* 6:915–921); direct gene transfer (Paszkowski et al. (1984) *EMBO J.* 3:2717–2722); and ballistic particle bombardment (see, for example, Sanford et al., U.S. Pat. No. 4,945,050; Tomes et al. (1995) in *Plant Cell, Tissue and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Biotechnology* 6:923–926 (soybean); Finer and McMullen (1991) *In Vitro Cell Dev. Biol.* 27P: 175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Klein et al. (1988) *Plant Physiol.* 91:440–444 (maize); Fromm et al. (1990) *Biotechnology* 8:833–839; and Tomes et al. (1995) in *Plant Cell, Tissue, and Organ Culture: Fundamental Methods*, ed. Gamborg and Phillips (Springer-Verlag, Berlin) (maize); Hooydaas-Van Slogteren and Hooykaas (1984) *Nature* (London) 311:763–764; Bytebier et al. (1987) *Proc. Natl. Acad. Sci. USA* 84:5345–5349 (Liliaceae); De Wet et al. (1985) in *The Experimental Manipulation of Ovule Tissues*, (G. H. P. Chapman et al., Longman, NY eds. pp. 197–209) (pollen); Kaeppler et al. (1990) *Plant Cell Reports* 9:415–418; Kaeppler et al. (1992) *Theor. Appl. Genet.* 84:560–566 (whisker-mediated transformation); DeHalluin et al. (1992) *Plant Cell* 4:1495–1505 (electroporation); Li et al. (1993) *Plant Cell Reports* 12:250–255, and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

Plant tissues suitable for transformation include but are not limited to leaf tissues, root tissues, shoots, meristems, and protoplasts. For soybean it is often preferred to utilize explants of cotyledons.

For example, the *Agrobacterium tumefaciens* strain A208 is known to be highly virulent on soybean and to give rise to a higher rate of transformation. See Byrne et al. (1987) *Plant Cell Tissue and Organ Culture* 8:3–15. The transformation of soybean protoplasts by co-culturing them with *Agrobacterium tumefciens* or *Agrobacterium rhizogenes* has been known and is hereby incorporated by reference. See Facciotti et al. (1985) *Biotechnology* (New York) 3:241. Tissue explants may be inoculated with the bacterium for transformation. For example, U.S. Pat. No. 5,569,834 issued to Hinchee et al. discloses a method for soybean transformation and regeneration by inoculating a cotyledon explant that is torn apart at the cotyledonary node.

Alternatively, plants can also be transformed successfully by the biolistic technique, which involves using high velocity microprojectiles carrying microparticles containing the transformation construct to propel the microparticles into a plant cell, protoplast, or tissue. The high velocity microprojectile penetrates the outer cell surface without destroying the cell and injects the microparticles into the cells. The transformation construct in the microparticles is thereafter released and incorporated into the cell genome. This technique is also known as particle bombardment and is disclosed in U.S. Pat. Nos. 4,945,050, 5,036,006, and 5,100,792, which are hereby incorporated by reference. The key advantage of this technique is that it works on virtually any plant tissue. An example of successful transformation of soybean using this particle bombardment technique is demonstrated in McCabe et al. (1988) *Biotechnology* 6:923–926.

In yet another method of transformation, protoplasts are transfected directly with expression vector DNA that contains the nematode-resistance gene by electroporation or DNA-protoplast co-precipitation in accordance with procedures generally known in the art. See Christou et al. (1987) *Proc. Natl. Acad. Sci. USA* 84:3962–3966; Lin et al. (1987) *Plant Physiol.* 84:856–861.

Once the transformation construct containing the isolated DNA sequences of this invention has been delivered, protoplasts, cells, or tissues expressing the protein encoded by the isolated nematode resistance gene are selected. Selection can be based on the selectable marker that is incorporated in the transformation construct or by culturing the protoplasts, cells, or tissues in media containing one of the antibiotics or herbicides. Alternatively, nematode-resistance may be directly selected by inoculating nematodes into the transformed protoplasts, cells, or tissues. Both methods of selection are generally known in the art.

A further aspect of the present invention relates to the regeneration of transgenic plants that express nematode resistance genes of the invention. The cells that have been transformed and selected for expression of the sequence of this invention may be grown into plants in accordance with conventional ways. See, for example, McCormick et al. (1986) *Plant Cell Reports* 5:81–84. These plants may then be grown, and either pollinated with the same transformed strain or different strains, the resulting hybrid having the desired genetic traits necessary for nematode-resistance.

For example, in soybean, transgenic soybean regeneration has been successful from tissues such as nodal axillary buds transformed with electroporation-mediated gene transfer technique (Chowrira et al. (1996) *Mol. Biotechnol.* 5:85–96); somatic embryos transformed using microprojectile bombardment (Stewart et al. (1996) *Plant Physiol.* 112:121–129); and cotyledon explants that are torn apart at the cotyledonary node and are transformed by Agrobacterium inoculation (U.S. Pat. No. 5,569,834 issued to Hinchee et al.). Other methods for regenerating soybean plants are disclosed in U.S. Pat. No. 4,684,612 issued to Hemphill et al., and U.S. Pat. No. 4,992,375 issued to Wright, which are hereby incorporated by reference.

The sequences of the invention are generally introduced into plants wherein the plant in its native state does not contain the DNA sequences. However, it is recognized that in some plants the gene may occur but does not confer resistance because of aberrant expression, a mutation in the sequence, a nonfunctional protein, and the like. It will be beneficial to transform such plants with the sequences of the invention.

Using cells and tissues of the present invention that are resistant to nematodes helps to obviate the problem of nematode infection of the host cells and tissues in the culture. In addition, the cells and tissues according to the present invention can also be valuable in the elucidation of the mechanism underlying the plant resistance to pathogens. Such plants include maize, oats, wheat, rice, barley, sorghum, alfalfa, tobacco, cotton, sugar beet, sunflower, carrot, canola, tomato, potato, oilseed rape, cabbage, pepper, lettuce, brassicas, tobacco, and soybean.

It is recognized that resistance to nematodes may be multigenic and quantitative in certain plants. Thus, the sequences disclosed herein may be useful alone or in combination with other sequences. Breeding programs have produced many genotypes that have varying numbers of the genes responsible for nematode resistance.

Thus, the isolated DNA sequences of the invention are preferably used to transform plants expressing one or more other nematode resistance genes. Such plants may be naturally occurring, produced by breeding programs, or produced by transformation with other nematode resistance genes. The result of the transformation with the isolated nematode resistance gene of this invention improves the plants capacity for nematode resistance.

Cotransformation may be conducted to introduce the DNA sequences of this invention into plants together with one or more other nematode resistance genes. In the transformation construct, the other known nematode resistance genes may be contained on the same plasmid as the DNA sequence of this invention or may be contained on a separate plasmid or DNA molecule. The methods for making transformation constructs having the other known nematode resistance gene with or without a DNA sequence isolated in this invention are similar to the methods described above and should be apparent to a person skilled in the art.

Several methods of cotransformation of plants have been developed. Cotransformation is easily accomplished by DNA mediated processes, such as the co-precipitation method, biolistic method, and electroporation. Each of these methods is adequately suited for the introduction of the DNA sequences of this invention and other nematode resistance genes, on the same or separate plasmids, into the plant cells. Alternatively, *Agrobacterium tumefaciens*-mediated cotransformation techniques can be employed. Examples of such techniques can be found in, for example, Depicker et al. (1985) *Mol. Gen. Genet.* 201:477–484; McKnight et al. (1987) *Plant Mol. Biol.* 8:439–445; De Block et al. (1991) *Theor. Appl. Genet.* 82:257–263; de Framond et al. (1986) *Mol. Gen. Genet.* 202:125–131; and Komari et al. (1996) *The Plant Journal* 10: 165–174. In an alternative method, multiple transgenes may be brought together by breeding of separately transformed parent plants.

The following examples are offered by way of illustration and not by way of limitation.

EXAMPLES

Example 1

Incorporation of DNA Sequences Conferring Nematode Resistance into Expression Vectors Genomic DNA sequences spanning the full length coding regions of gene fragments conferring nematode-resistance to maize and soybean were isolated and cloned. These sequences are set forth in SEQ ID NOs: 1 and 3 (maize) and 5 and 7 (soybean). Plasmids containing these sequences have been deposited with American Type Culture Collection (ATCC) on Oct. 15, 1997, and on Feb. 4, 1998 and are assigned Accession Numbers 209366, 209365, 209614, 209363, and 209364.

Gene fragments are cloned into a plasmid vector, such as that shown in FIG. 1, in the sense orientation so that they are under the transcriptional control of a constitutive promoter. The transformation construct is then available for introduction into soybean cells by bombardment methods as described in Example 2.

Example 2

Transformation of Soybean Cells and Regeneration of Transgenic Plants Having Improved Nematode Resistance Initiation and Maintenance of Embryogenic Suspension Cultures Embryogenic suspension cultures of soybean (Glycine max Merrill) are initiated and maintained in a 10A40N medium supplemented with 5 mM asparagine as described previously (Finer and Nagasowa (1988) *Plant Cell Tissue Org. Cult.* 15:125–136). For subculture, two clumps of embryogenic tissue, 4 mm in diameter, are transferred to 35 ml of 10A40N medium in a 125-ml delong flask. High quality embryogenic material is selectively subcultured monthly at this low inoculum density.

Preparation of DNA and Tungsten Pellets

Plasmid DNA from Example 1 is precipitated onto 1.1 μm (average diameter) tungsten pellets using a $CaCl_2$ precipitation procedure (Finer and McMullen (1990) *Plant Cell Rep.* 8:586–589). The pellet mixture containing the precipitated DNA is gently resuspended after precipitation, and 2 μl is removed for bombardment.

Preparation of Plant Tissue for Bombardment

Approximately 1 g of embryogenic suspension culture tissue (taken 3 weeks after subculture) is transferred to a 3.5-cm-diameter petri dish. The tissue is centered in the dish, the excess liquid is removed with a pipette, and a sterile 500 μm pore size nylon screen (Tetko Inc., Elmsford, N.Y.) is placed over the embryonic tissue. Open petri dishes are placed in a laminar-flow hood for 10 to 15 minutes to evaporate residual liquid medium from the tissue. The 3.5-cm-diameter petri dish is placed in the center of a 9-cm-diameter petri dish immediately before bombardment. Bombardments are performed using a DuPont Biolistics Particle Delivery System (model BPG). Each sample of embryogenic soybean tissue is bombarded once.

Selection for Transgenic Clones

Bombarded tissues are resuspended in the 10A40N maintenance medium. One to two weeks after bombardment the clumps of embryogenic tissue are resuspended in fresh 10A40N medium containing a selection agent, such as kanomycin or hygromycin. The selection agent is filter-sterilized before addition to liquid media. The medium containing a selection agent is replaced with fresh antibiotic-containing medium weekly for 3 additional weeks.

Six to eight weeks after the initial bombardment, brown clumps of tissue that contain yellow-green lobes of embryogenic tissue are removed and separately subcultured in 10A40N medium containing selection agent. After 3 to 4 months of maintenance in this medium, proliferating embryogenic tissues are maintained by standard subculture in 10A40N without added antibiotic. Embryogenic tissues are periodically removed from 10A40N medium containing selection agent and 10A40N for embryo development and Southern hybridization analyses.

Embryo Development and Germination

For embryo development, clumps of kanamycin-resistant embryogenic tissues are placed at 23° C. on the embryo development medium, which contains MS salts (Murashige and Skoog (1962) *Physiol. Plant* 15:474–497), B5 vitamins (Gamborg et al. (1968) *Exp. Cell. Res.* 50:151–158), 6% maltose, and 0.2% gelrite (pH 5.7). One month after plating, the developing embryos are cultured as individual embryos, 25 per 9-cm-diameter petri dish in fresh embryo development medium. After an additional 4 weeks, the mature embryos are placed in dry petri dishes for 2 to 3 days. After the desiccation treatment, the embryos are transferred to a medium containing MS salts, B5 vitamins, 3% sucrose, and 0.2% Gelrite (pH 5.7). After root and shoot elongation, plantlets are transferred to pots containing a 1:1:1 mixture of vermiculite, topsoil, and peat, and maintained under high humidity. Plantlets are gradually exposed to ambient humidity over a 2-week period and placed in the greenhouse, where they are grown to maturity and monitored for expression of the nematode resistance gene.

DNA Extraction and Southern Hybridization Analysis

DNA is extracted from embryogenic tissue and leaves using the CTAB procedure (Saghai-Maroofet al. (1984) *Proc. Natl. Acad. Sci. USA* 81:8014–8018). Digested DNAs are electrophoresed on a 0.8% agarose gel. The DNA in the gels is treated with 0.2 N HCl, twice for 15 minutes, followed with 0.5 M NaOH/0. 1 M 1.5 M NaCl, twice for 30 minutes, and finally 1 M $NH_4C_2H_3O_2$/0.1 M NaOH, for 40 minutes. The DNA is transferred (Vollrath et al. (1988) *Proc. Natl. Acad. Sci. USA* 85:6027–6031) to nylon membranes (Zetaprobe-BioRad, Richmond, Calif.) overnight by capillary transfer using 1 M $NH_4C_2H_3O_2$/0.1 M NaOH. The membranes are baked at 80° C. for 2 hours under vacuum and then prehybridized for 4 to 6 hours at 65° C. in 50 mM Tris.pH 8.0, 5×standard saline citrate (SSC), 2×Denhardt's, 10 mM $Na_2EDTA$, 0.2% sodium dodecyl sulfate (SDS), and 62.5 μg/ml salmon sperm DNA.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated protein involved in nematode resistance, said protein comprising an amino acid sequence selected from the group consisting of the sequences set forth in SEQ ID NO: 2, SEQ ID NO: 4, SEQ ID NO: 6, and SEQ ID NO: 8.

2. An isolated protein comprising an amino acid sequence selected from the group consisting of:
   a) an amino acid sequence set forth in SEQ ID NO: 2, SEQ ID NO: 4, SEQ ID NO: 6, or SEQ ID NO: 8; and
   b) an amino acid sequence encoded by a nucleotide sequence contained in a plasmid having ATCC accession number 209366, 209365, 209614, 209363, 209364, wherein said isolated protein is involved in nematode resistance.

3. An isolated protein comprising an amino acid sequence set forth in SEQ ID NO: 2, SEQ ID NO: 4, SEQ ID NO: 6, or SEQ ID NO: 8 with at least one conservative amino acid substitution, and wherein said isolated protein has the same nucleotide resistance property as that of the amino acid sequence set forth in SEQ ID NO: 2, SEQ ID NO: 4, SEQ ID NO: 6, or SEQ ID NO: 8.

4. An isolated protein comprising an amino acid sequence having at least 90% sequence identity to an amino acid sequence selected from the group consisting of:
   a) an amino acid sequence set forth in SEQ ID NO: 2, SEQ ID NO: 4, SEQ ID NO: 6, or SEQ ID NO: 8; and
   b) an amino acid sequence encoded by a nucleotide sequence contained in a plasmid having ATCC accession number 209366, 209365, 209614, 209363, 209364;

wherein said isolated protein has the same nucleotide resistance property as that of the amino acid sequence set forth in SEQ ID NO: 2, SEQ ID NO: 4, SEQ ID NO: 6, or SEQ ID NO: 8.

* * * * *

UNITED STATES PATENT AND TRADEMARK OFFICE
CERTIFICATE OF CORRECTION

PATENT NO. : 6,228,992 B1  
DATED : May 8, 2001  
INVENTOR(S) : Jessen et al.

Page 1 of 1

It is certified that error appears in the above-identified patent and that said Letters Patent is hereby corrected as shown below:

Title page,
"PROTEINS" should read -- GENES AND METHODS --.

Column 41, claim 2,
Line 52, after "209363" insert -- or --.

Column 41, claim 3,
Line 57, cancel "and"; column 42, line 39 "nucleotide" should read -- nematode --.

Column 42, claim 4,
Line 50, after "209363" insert -- or --; line 52, "nucleotide" should read -- nematode --.

Signed and Sealed this

Eighth Day of January, 2002

Attest:

JAMES E. ROGAN
*Attesting Officer*  *Director of the United States Patent and Trademark Office*

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1347 base pairs
      (B) TYPE: nucleic acid
      (C) STRANDEDNESS: single
      (D) TOPOLOGY: linear -continued (ii) MOLECULE TYPE: cDNA (vi) ORIGINAL SOURCE:
    (A) ORGANISM: Zea mays (vii) IMMEDIATE SOURCE:
    (B) CLONE: P12217

(ix) FEATURE:
    (A) NAME/KEY: CDS
    (B) LOCATION: 146..994

(xi) SEQUENCE DESCRIPTION: SEQ ID NO:1:

```
CCACGCGTCC GCGGACGCGT GGGTGCCCGG GAGCGCCGCC GCGGTCGTGT GCCAGGTCAG       60

CGAGGCCAGC CTGCTCCCGC GCCTCGCCGC GTGGGACAAG TCCGAGACGC TCGCGGCCAA      120

GATCATGTAC GCCATCGAGA GCCAG ATG CAG GGC TGC GCC TTC ACG CTC GGA       172
                           Met Gln Gly Cys Ala Phe Thr Leu Gly
                             1               5

CTC GGC GAG CCC AAC CTC GCC GGC AAG CCC GTG CTC GAG TAC GAC CGC       220
Leu Gly Glu Pro Asn Leu Ala Gly Lys Pro Val Leu Glu Tyr Asp Arg
 10              15                  20                  25

GTC GTG CGC CCG CAC GAG CTG CAC GCG CTC AAG CCC AAG CCA GCG CCG       268
Val Val Arg Pro His Glu Leu His Ala Leu Lys Pro Lys Pro Ala Pro
                 30                  35                  40

GAG CCC AAG TCT GGG TAC CTC AAC AGG GAG AAC GAG ACG CTG TTC ACC       316
Glu Pro Lys Ser Gly Tyr Leu Asn Arg Glu Asn Glu Thr Leu Phe Thr
                 45                  50                  55

ATG TAC CAG ATA CTC GAA TCG TGG CTG CGC GCC GCG TCG CAA CTC CTC       364
Met Tyr Gln Ile Leu Glu Ser Trp Leu Arg Ala Ala Ser Gln Leu Leu
             60                  65                  70

GCC CGC CTC AAC GAA CGG ATC GAA GCC AAG AAC TGG GAA GCG GCG GCT       412
Ala Arg Leu Asn Glu Arg Ile Glu Ala Lys Asn Trp Glu Ala Ala Ala
 75                  80                  85

GCC GAC TGC TGG ATC CTG GAG CGC GTG TGG AAG CTG CTC GCC GAC GTC       460
Ala Asp Cys Trp Ile Leu Glu Arg Val Trp Lys Leu Leu Ala Asp Val
 90                  95                 100                 105

GAG GAC CTC CAC CTG CTG ATG GAC CCG GAC GAC TTC CTG CGG CTC AAG       508
Glu Asp Leu His Leu Leu Met Asp Pro Asp Asp Phe Leu Arg Leu Lys
                110                 115                 120

GGC CAG CTC GCT GTA CGA GCG GCT CCA TGG TCT GAC GCG TCG TTC TGT       556
Gly Gln Leu Ala Val Arg Ala Ala Pro Trp Ser Asp Ala Ser Phe Cys
             125                 130                 135

TTC CGG TCC AGG GCG CTC CTG CAC GTC GCT AAC ACC ACT AGG GAC CTC       604
Phe Arg Ser Arg Ala Leu Leu His Val Ala Asn Thr Thr Arg Asp Leu
            140                 145                 150

AAG AAG CGT GTG CCC TGG GTG CTC GGT GTC GAG GTG GAC CCC AAC GGC       652
Lys Lys Arg Val Pro Trp Val Leu Gly Val Glu Val Asp Pro Asn Gly
155                 160                 165

GGC CCG CGG GTG CAG GAG GCA GCC ATG ATG CTG TAC CAC AGC CGT AGG       700
Gly Pro Arg Val Gln Glu Ala Ala Met Met Leu Tyr His Ser Arg Arg
170                 175                 180                 185

CGC GGC GAG GGC GAG GAG GCG GGC AAG GTG GAG CTG CTC CAG GCC TTC       748
Arg Gly Glu Gly Glu Glu Ala Gly Lys Val Glu Leu Leu Gln Ala Phe
                190                 195                 200

CAA GCA GTG GAG GTG GCC GTG AGA GGA TTC TTC TTC GCG TAC CGG CAG       796
Gln Ala Val Glu Val Ala Val Arg Gly Phe Phe Phe Ala Tyr Arg Gln
            205                 210                 215

CTC GTG GCG GCG GTG ATG GGC ACG GCG GAG GCG TTG GGC AAC CGG GCG       844
Leu Val Ala Ala Val Met Gly Thr Ala Glu Ala Leu Gly Asn Arg Ala
            220                 225                 230
```

```
CTG TTC GTG CCG GCG GAG GGG ATG GAT CCA TTG GCC CAG ATG TTC CTC         892
Leu Phe Val Pro Ala Glu Gly Met Asp Pro Leu Ala Gln Met Phe Leu
    235                 240                 245

GAG CCA CCC TAC TAC CCC AGC CTG GAT GCC GCC AAG ACG TTC CTA GCG         940
Glu Pro Pro Tyr Tyr Pro Ser Leu Asp Ala Ala Lys Thr Phe Leu Ala
250                 255                 260                 265

GAT TAC TGG GTT CAG CAG ATG GCG GGG GCC TCT GCT CCG TCA ATA CAA         988
Asp Tyr Trp Val Gln Gln Met Ala Gly Ala Ser Ala Pro Ser Ile Gln
                    270                 275                 280

AGC TGA AACGGCAAA TGGCGCGGCT GGATAGCGAC CGAATCGCGC AGTTTTGCAG          1044
Ser *

CCTGAAGATA CTATGTATGC ATGCATCGTA ATTTCGCTGT GGCCTTGTGG TGATAGAGTG      1104

ATTCATTTCT ATAGCGATCC TGTACTAGTG TAGTACATGT AGCACTAAAT TGTCTTATTA      1164

TCGTTGTGCT TGTGCACTGC GTTGTGTTGT GTTCTACATA GAGATTGATT CAGTTAGATG      1224

CCATTTGTCA CTCTAGGCAA GTGTTTCAAT TGGGCACCGT GTATATATAG AACTTTTGTA      1284

AACACTGGTA GATGGATTCA TCAATTACAG AATGTTGATG TTGACAAAAA AAAAAAAAAA      1344

AAA                                                                    1347

(2) INFORMATION FOR SEQ ID NO:2:

(i) SEQUENCE CHARACTERISTICS:
        (A) LENGTH: 282 amino acids
        (B) TYPE: amino acid
        (D) TOPOLOGY: linear (ii) MOLECULE TYPE: protein (xi) SEQUENCE DESCRIPTION: SEQ ID NO:2:

Met Gln Gly Cys Ala Phe Thr Leu Gly Leu Gly Glu Pro Asn Leu Ala
 1               5                  10                  15

Gly Lys Pro Val Leu Glu Tyr Asp Arg Val Val Arg Pro His Glu Leu
                20                  25                  30

His Ala Leu Lys Pro Lys Pro Ala Pro Glu Pro Lys Ser Gly Tyr Leu
            35                  40                  45

Asn Arg Glu Asn Glu Thr Leu Phe Thr Met Tyr Gln Ile Leu Glu Ser
        50                  55                  60

Trp Leu Arg Ala Ala Ser Gln Leu Leu Ala Arg Leu Asn Glu Arg Ile
 65                 70                  75                  80

Glu Ala Lys Asn Trp Glu Ala Ala Ala Asp Cys Trp Ile Leu Glu
                85                  90                  95

Arg Val Trp Lys Leu Leu Ala Asp Val Glu Asp Leu His Leu Met
                100                 105                 110

Asp Pro Asp Asp Phe Leu Arg Leu Lys Gly Gln Leu Ala Val Arg Ala
            115                 120                 125

Ala Pro Trp Ser Asp Ala Ser Phe Cys Phe Arg Ser Arg Ala Leu Leu
        130                 135                 140

His Val Ala Asn Thr Thr Arg Asp Leu Lys Lys Arg Val Pro Trp Val
145                 150                 155                 160

Leu Gly Val Glu Val Asp Pro Asn Gly Gly Pro Arg Val Gln Glu Ala
                165                 170                 175

Ala Met Met Leu Tyr His Ser Arg Arg Arg Gly Glu Gly Glu Glu Ala
            180                 185                 190

Gly Lys Val Glu Leu Leu Gln Ala Phe Gln Ala Val Glu Val Ala Val
        195                 200                 205
```

```
Arg Gly Phe Phe Phe Ala Tyr Arg Gln Leu Val Ala Ala Val Met Gly
    210                 215                 220

Thr Ala Glu Ala Leu Gly Asn Arg Ala Leu Phe Val Pro Ala Glu Gly
225                 230                 235                 240

Met Asp Pro Leu Ala Gln Met Phe Leu Glu Pro Pro Tyr Tyr Pro Ser
                245                 250                 255

Leu Asp Ala Ala Lys Thr Phe Leu Ala Asp Tyr Trp Val Gln Gln Met
            260                 265                 270

Ala Gly Ala Ser Ala Pro Ser Ile Gln Ser
        275                 280

(2) INFORMATION FOR SEQ ID NO:3:

(i) SEQUENCE CHARACTERISTICS:
        (A) LENGTH: 1325 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Zea mays (vii) IMMEDIATE SOURCE:
        (B) CLONE: P12218

(ix) FEATURE:
        (A) NAME/KEY: CDS
        (B) LOCATION: 126..983

(xi) SEQUENCE DESCRIPTION: SEQ ID NO:3:

CCACGCGTCC GAGCGCCGCC GCGGTCGTGT GCCGGGCCAG CAAGGCCAGC CTGCTCCCGC       60

GCCTCGCCGC GTGGGAGAAG TCTGAGGCGC TCGCGGCCAG GATCACGTAC GCCGTCGAGG      120

GCCAG ATG CAG GGC TGC GCC TTC ACG CTC GGC CTC GGC GAG CCC AAC         167
      Met Gln Gly Cys Ala Phe Thr Leu Gly Leu Gly Glu Pro Asn
          285                 290                 295

CTC GCC GGC AAG CCC GTG CTC GAG TAC GAC CGC GTC GTG CGC CCG CAC       215
Leu Ala Gly Lys Pro Val Leu Glu Tyr Asp Arg Val Val Arg Pro His
        300                 305                 310

GAG CTG CAC GCG CTG AAG CCC GAC CCT GCG CCG GAG CCC ATG TCC GGC       263
Glu Leu His Ala Leu Lys Pro Asp Pro Ala Pro Glu Pro Met Ser Gly
    315                 320                 325

TAC CGC AAC CGG GAG CTC GAG ACT CTG TTC ACC ATG TAC CAG ATA CTC       311
Tyr Arg Asn Arg Glu Leu Glu Thr Leu Phe Thr Met Tyr Gln Ile Leu
330                 335                 340                 345

GAG TCC TGG CTC CGC GTC GCG TCG CAG CTG CTC ACC CGC CTC GAC GAG       359
Glu Ser Trp Leu Arg Val Ala Ser Gln Leu Leu Thr Arg Leu Asp Glu
            350                 355                 360

CGG ATC GAA GAC AAG TGC TGG GAG GCG GCG GCC GGC GAC TGC TGG ATC       407
Arg Ile Glu Asp Lys Cys Trp Glu Ala Ala Ala Gly Asp Cys Trp Ile
            365                 370                 375

CTG GAG CGC GTG TGG AAG CTG CTC GCG GAC GTC GAG GAC CTC CAC CTG       455
Leu Glu Arg Val Trp Lys Leu Leu Ala Asp Val Glu Asp Leu His Leu
            380                 385                 390

CTG ATG GAC CCG GAC GAG TTC CTA CGG CTC AAG AGC CAG CTC GCC GTA       503
Leu Met Asp Pro Asp Glu Phe Leu Arg Leu Lys Ser Gln Leu Ala Val
    395                 400                 405

CGA GCG GCG CCG GGG TCT GAG TCC GCG TCC TTC TGT TTC CGG TCC ACG       551
Arg Ala Ala Pro Gly Ser Glu Ser Ala Ser Phe Cys Phe Arg Ser Thr
410                 415                 420                 425
```

```
GCG CTC CTG CAC GTC GCT AGC GCC ACT AGG GAC CTC AAG AAG CGT GTG      599
Ala Leu Leu His Val Ala Ser Ala Thr Arg Asp Leu Lys Lys Arg Val
            430                 435                 440

CCC TGG GTG CTC GGT GTC GAG GCG GAC CCC AGC GGC GGC CCA CGG GTG      647
Pro Trp Val Leu Gly Val Glu Ala Asp Pro Ser Gly Gly Pro Arg Val
            445                 450                 455

CAG GAG GCG GCC ATG AAG CTG TAC CAC AGC CGT AGG CGC GGT GAG GGC      695
Gln Glu Ala Ala Met Lys Leu Tyr His Ser Arg Arg Arg Gly Glu Gly
            460                 465                 470

GAG GAG GCA GGC AAG GTG GAC CTG CTC CAG GCC TTC CAG GCG GTG GAG      743
Glu Glu Ala Gly Lys Val Asp Leu Leu Gln Ala Phe Gln Ala Val Glu
            475                 480                 485

GTG GCC GTG AGA GCA TTC TTC TTC GGG TAC CGG CAG CTG GTG GCG GCG      791
Val Ala Val Arg Ala Phe Phe Phe Gly Tyr Arg Gln Leu Val Ala Ala
490                 495                 500                 505

GTG ATG GGC ACG GCG GAG GCG TCG GGC AAC CGG GCG CTG TTC GTG CCG      839
Val Met Gly Thr Ala Glu Ala Ser Gly Asn Arg Ala Leu Phe Val Pro
            510                 515                 520

GCG GAG GAG ATG GAT CCG CTC GCC CAA ATG TTC CTG GAG CCG CCA TAC      887
Ala Glu Glu Met Asp Pro Leu Ala Gln Met Phe Leu Glu Pro Pro Tyr
            525                 530                 535

TAC CCT AGC CTG GAC GCC GCC AAG ACG TTT CTA GCG GAT TAC TGG GTT      935
Tyr Pro Ser Leu Asp Ala Ala Lys Thr Phe Leu Ala Asp Tyr Trp Val
            540                 545                 550

CAG CTT CAG CAG ATG GCG GAG GCC TCT GCT CCG TCA AGA CAA AGC TGA      983
Gln Leu Gln Gln Met Ala Glu Ala Ser Ala Pro Ser Arg Gln Ser  *
            555                 560                 565

AACGGCGAAA TGGCACGGCT GAGCCACCGA ATCGCGCAGT TTTGCAGGAC TGAAGATACT   1043

ATGCATGCAT TTCGTTGGGG CCTTTTGCCC TTGTGGTGAA TGGTGATAGA GTGATTCATT   1103

TCTATAGCGA TCATGTACTA TTGCAGTACA TGTCGCACTA GAATACTAGA TTCTCTTACT   1163

ATCGTTGTGC ACTGCGTTGT ACGTGTTGTG TTCTACGTAG ATATAGATTG ATTCAGTTAG   1223

ATGTCATTTG TATTGCCAAG TAGGTCAATT GGATATGGAA CTTTTGTAAA TACCGAAATA   1283

CTGTTGTTGA AAAAAAAAA AAAAAAAAA AAAAAAAAA AA                        1325

(2) INFORMATION FOR SEQ ID NO:4:

(i) SEQUENCE CHARACTERISTICS:
        (A) LENGTH: 285 amino acids
        (B) TYPE: amino acid
        (D) TOPOLOGY: linear (ii) MOLECULE TYPE: protein (xi) SEQUENCE DESCRIPTION: SEQ ID NO:4:

Met Gln Gly Cys Ala Phe Thr Leu Gly Leu Gly Glu Pro Asn Leu Ala
 1               5                  10                  15

Gly Lys Pro Val Leu Glu Tyr Asp Arg Val Val Arg Pro His Glu Leu
            20                  25                  30

His Ala Leu Lys Pro Asp Pro Ala Pro Glu Pro Met Ser Gly Tyr Arg
            35                  40                  45

Asn Arg Glu Leu Glu Thr Leu Phe Thr Met Tyr Gln Ile Leu Glu Ser
        50                  55                  60

Trp Leu Arg Val Ala Ser Gln Leu Leu Thr Arg Leu Asp Glu Arg Ile
65                  70                  75                  80

Glu Asp Lys Cys Trp Glu Ala Ala Ala Gly Asp Cys Trp Ile Leu Glu
                85                  90                  95
```

```
Arg Val Trp Lys Leu Leu Ala Asp Val Glu Asp Leu His Leu Leu Met
            100                 105                 110

Asp Pro Asp Glu Phe Leu Arg Leu Lys Ser Gln Leu Ala Val Arg Ala
            115                 120                 125

Ala Pro Gly Ser Glu Ser Ala Ser Phe Cys Phe Arg Ser Thr Ala Leu
130                 135                 140

Leu His Val Ala Ser Ala Thr Arg Asp Leu Lys Lys Arg Val Pro Trp
145                 150                 155                 160

Val Leu Gly Val Glu Ala Asp Pro Ser Gly Gly Pro Arg Val Gln Glu
                165                 170                 175

Ala Ala Met Lys Leu Tyr His Ser Arg Arg Arg Gly Glu Gly Glu Glu
            180                 185                 190

Ala Gly Lys Val Asp Leu Leu Gln Ala Phe Gln Ala Val Glu Val Ala
            195                 200                 205

Val Arg Ala Phe Phe Phe Gly Tyr Arg Gln Leu Val Ala Ala Val Met
            210                 215                 220

Gly Thr Ala Glu Ala Ser Gly Asn Arg Ala Leu Phe Val Pro Ala Glu
225                 230                 235                 240

Glu Met Asp Pro Leu Ala Gln Met Phe Leu Glu Pro Pro Tyr Tyr Pro
                245                 250                 255

Ser Leu Asp Ala Ala Lys Thr Phe Leu Ala Asp Tyr Trp Val Gln Leu
            260                 265                 270

Gln Gln Met Ala Glu Ala Ser Ala Pro Ser Arg Gln Ser
            275                 280                 285

(2) INFORMATION FOR SEQ ID NO:5:

(i) SEQUENCE CHARACTERISTICS:
        (A) LENGTH: 1498 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Glycine max (vii) IMMEDIATE SOURCE:
        (B) CLONE: P12568

(ix) FEATURE:
        (A) NAME/KEY: CDS
        (B) LOCATION: 69..1436

(xi) SEQUENCE DESCRIPTION: SEQ ID NO:5:

CGACACCAAT TTCTCCATCC TCTCATTGAA AAACAAAATT AATCATCTTA CTTATTTATT      60

CTCCGAAA ATG GTT GAT TTA CAT TGG AAA TCA AAG ATG CCA AGT TCC GAC     110
         Met Val Asp Leu His Trp Lys Ser Lys Met Pro Ser Ser Asp
                 290                 295                 300

ATG CCT TCC AAA ACT CTA AAA CTC TCT CTC TCC GAC AAC AAG TCC TTA     158
Met Pro Ser Lys Thr Leu Lys Leu Ser Leu Ser Asp Asn Lys Ser Leu
                305                 310                 315

CCC TCT TTG CAA CTA CCC TTC CGC ACC ACA GAT ATC TCT CAC GCC GCA     206
Pro Ser Leu Gln Leu Pro Phe Arg Thr Thr Asp Ile Ser His Ala Ala
                320                 325                 330

CCT TCT GTT TGC GCC ACT TAC GAC TAC TAT CTC CGT CTT CCT CAA CTC     254
Pro Ser Val Cys Ala Thr Tyr Asp Tyr Tyr Leu Arg Leu Pro Gln Leu
                335                 340                 345
```

```
AGA AAG CTT TGG AAC TCC TCA GAT TTT CCT AAT TGG AAC AAC GAA CCA      302
Arg Lys Leu Trp Asn Ser Ser Asp Phe Pro Asn Trp Asn Asn Glu Pro
    350                 355                 360

ATC TTA AAA CCT ATC TTG CAA GCT CTC GAA ATC ACC TTC CGC TTT CTC      350
Ile Leu Lys Pro Ile Leu Gln Ala Leu Glu Ile Thr Phe Arg Phe Leu
365                 370                 375                 380

TCC ATT GTT CTC TCC GAT CCA AGA CCT TAC TCC AAC CAC AGA GAA TGG      398
Ser Ile Val Leu Ser Asp Pro Arg Pro Tyr Ser Asn His Arg Glu Trp
                385                 390                 395

ACT CGC AGG ATA GAG TCT CTT ATC ACA CAT CAA ATT GAA ATC ATT GCC      446
Thr Arg Arg Ile Glu Ser Leu Ile Thr His Gln Ile Glu Ile Ile Ala
            400                 405                 410

ATA CTT TGT GAA GAT GAG GAA CAA AAT TCC GAC ACA CGT GGC ACT GCA      494
Ile Leu Cys Glu Asp Glu Glu Gln Asn Ser Asp Thr Arg Gly Thr Ala
            415                 420                 425

CCA ACC GCT GAT CTC AGC AGG AAC AAT AGC AGC GAG AGC AGA AGC TAC      542
Pro Thr Ala Asp Leu Ser Arg Asn Asn Ser Ser Glu Ser Arg Ser Tyr
        430                 435                 440

AGC GAG GCA AGC CTG CTT CCG CGG CTT GCC ACG TGG TAC AAA TCC AAG      590
Ser Glu Ala Ser Leu Leu Pro Arg Leu Ala Thr Trp Tyr Lys Ser Lys
445                 450                 455                 460

GAC GTA GCG CAG AGG ATC CTT CTC TCA GTT GAA TGC CAA ATG AGG AGG      638
Asp Val Ala Gln Arg Ile Leu Leu Ser Val Glu Cys Gln Met Arg Arg
                465                 470                 475

TGT TCC TAC ACG CTG GGT TTG GGT GAG CCG AAC CTA GCG GGC AAA CCG      686
Cys Ser Tyr Thr Leu Gly Leu Gly Glu Pro Asn Leu Ala Gly Lys Pro
            480                 485                 490

AGC CTG CTC TAC GAC CTC GTG TGT AAG CCG AAC GAG ATC CAC GCG CTG      734
Ser Leu Leu Tyr Asp Leu Val Cys Lys Pro Asn Glu Ile His Ala Leu
        495                 500                 505

AAG ACG ACG CCG TAC GAT GAG CGC GTA GAG AAT CAC GAG AAC CAC GCG      782
Lys Thr Thr Pro Tyr Asp Glu Arg Val Glu Asn His Glu Asn His Ala
510                 515                 520

TTG CAC GCG ACG CAC CAG ATC GCC GAG TCG TGG ATC CAC GCG TCG CGG      830
Leu His Ala Thr His Gln Ile Ala Glu Ser Trp Ile His Ala Ser Arg
525                 530                 535                 540

AAG GTT CTA GAG AGG ATC GCA GAC GCG GTG CTC TCC AGA ACC TTC GAG      878
Lys Val Leu Glu Arg Ile Ala Asp Ala Val Leu Ser Arg Thr Phe Glu
                545                 550                 555

AAG GCG GCT GAG GAC TGC TAC GCC GTG GAA AGG ATC TGG AAG CTT CTC      926
Lys Ala Ala Glu Asp Cys Tyr Ala Val Glu Arg Ile Trp Lys Leu Leu
            560                 565                 570

GCG GAG GTG GAG GAC CTC CAC CTG ATG ATG GAT CCG GAC GAT TTC TTG      974
Ala Glu Val Glu Asp Leu His Leu Met Met Asp Pro Asp Asp Phe Leu
        575                 580                 585

AGA CTG AAG AAT CAG CTC TCG GTG AAA TCC TCC GGC GGC GAA ACG GCT     1022
Arg Leu Lys Asn Gln Leu Ser Val Lys Ser Ser Gly Gly Glu Thr Ala
590                 595                 600

TCG TTC TGC TTC AGG TCG AAG GAG TTG GTT GAA CTG ACG AAG ATG TGC     1070
Ser Phe Cys Phe Arg Ser Lys Glu Leu Val Glu Leu Thr Lys Met Cys
605                 610                 615                 620

AGA GAT CTG AGG CAC AAG GTG CCG GAG ATA TTG GAG GTG GAG GTG GAT     1118
Arg Asp Leu Arg His Lys Val Pro Glu Ile Leu Glu Val Glu Val Asp
                625                 630                 635

CCG AAG GGA GGA CCG AGG ATT CAA GAG GCG GCG ATG AAG CTC TAC GTT     1166
Pro Lys Gly Gly Pro Arg Ile Gln Glu Ala Ala Met Lys Leu Tyr Val
            640                 645                 650

TCG AAG AGC GCG TTC GAG AAG GTT CAC TTG TTG CAG GCG ATG CAG GCG     1214
Ser Lys Ser Ala Phe Glu Lys Val His Leu Leu Gln Ala Met Gln Ala
        655                 660                 665
```

```
ATT GAG GCG GCG ATG AAG AGA TTC TTC TAC GCG TAT AAG CAG GTG TTG      1262
Ile Glu Ala Ala Met Lys Arg Phe Phe Tyr Ala Tyr Lys Gln Val Leu
        670                 675                 680

GCG GTG GTG ATG GGA AGC TCC GAG GCT AAC GGT AAC CGA GTT GGG TTG      1310
Ala Val Val Met Gly Ser Ser Glu Ala Asn Gly Asn Arg Val Gly Leu
685                 690                 695                 700

AGT TGC GAC TCG GCT GAC TCG TTG ACT CAG ATT TTC CTT GAA CCG ACG      1358
Ser Cys Asp Ser Ala Asp Ser Leu Thr Gln Ile Phe Leu Glu Pro Thr
                705                 710                 715

TAT TTT CCA AGC TTG GAT GCC GCC AAG ACT TTT CTT GGA TAC TTG TGG      1406
Tyr Phe Pro Ser Leu Asp Ala Ala Lys Thr Phe Leu Gly Tyr Leu Trp
                720                 725                 730

GAT AAT AAC GAT AAT AAC AAA TGG ATA TGA TAAGGGAAAA AAAAAAACG         1456
Asp Asn Asn Asp Asn Asn Lys Trp Ile *
            735                 740

GCACAAAAAC GATGGCCAAA GTGAGATTTT CGGTTTGGGC AC                        1498

(2) INFORMATION FOR SEQ ID NO:6:

(i) SEQUENCE CHARACTERISTICS:
        (A) LENGTH: 455 amino acids
        (B) TYPE: amino acid
        (D) TOPOLOGY: linear (ii) MOLECULE TYPE: protein (xi) SEQUENCE DESCRIPTION: SEQ ID NO:6:

Met Val Asp Leu His Trp Lys Ser Lys Met Pro Ser Ser Asp Met Pro
1               5                   10                  15

Ser Lys Thr Leu Lys Leu Ser Leu Ser Asp Asn Lys Ser Leu Pro Ser
                20                  25                  30

Leu Gln Leu Pro Phe Arg Thr Thr Asp Ile Ser His Ala Ala Pro Ser
            35                  40                  45

Val Cys Ala Thr Tyr Asp Tyr Tyr Leu Arg Leu Pro Gln Leu Arg Lys
        50                  55                  60

Leu Trp Asn Ser Ser Asp Phe Pro Asn Trp Asn Asn Glu Pro Ile Leu
65                  70                  75                  80

Lys Pro Ile Leu Gln Ala Leu Glu Ile Thr Phe Arg Phe Leu Ser Ile
                85                  90                  95

Val Leu Ser Asp Pro Arg Pro Tyr Ser Asn His Arg Glu Trp Thr Arg
            100                 105                 110

Arg Ile Glu Ser Leu Ile Thr His Gln Ile Glu Ile Ala Ile Leu
        115                 120                 125

Cys Glu Asp Glu Glu Gln Asn Ser Asp Thr Arg Gly Thr Ala Pro Thr
130                 135                 140

Ala Asp Leu Ser Arg Asn Asn Ser Ser Glu Ser Arg Ser Tyr Ser Glu
145                 150                 155                 160

Ala Ser Leu Leu Pro Arg Leu Ala Thr Trp Tyr Lys Ser Lys Asp Val
                165                 170                 175

Ala Gln Arg Ile Leu Leu Ser Val Glu Cys Gln Met Arg Arg Cys Ser
            180                 185                 190

Tyr Thr Leu Gly Leu Gly Glu Pro Asn Leu Ala Gly Lys Pro Ser Leu
        195                 200                 205

Leu Tyr Asp Leu Val Cys Lys Pro Asn Glu Ile His Ala Leu Lys Thr
    210                 215                 220

Thr Pro Tyr Asp Glu Arg Val Glu Asn His Glu Asn His Ala Leu His
225                 230                 235                 240
```

```
Ala Thr His Gln Ile Ala Glu Ser Trp Ile His Ala Ser Arg Lys Val
            245                 250                 255

Leu Glu Arg Ile Ala Asp Ala Val Leu Ser Arg Thr Phe Glu Lys Ala
            260                 265                 270

Ala Glu Asp Cys Tyr Ala Val Glu Arg Ile Trp Lys Leu Leu Ala Glu
            275                 280                 285

Val Glu Asp Leu His Leu Met Met Asp Pro Asp Phe Leu Arg Leu
            290                 295                 300

Lys Asn Gln Leu Ser Val Lys Ser Ser Gly Gly Glu Thr Ala Ser Phe
305                 310                 315                 320

Cys Phe Arg Ser Lys Glu Leu Val Glu Leu Thr Lys Met Cys Arg Asp
                325                 330                 335

Leu Arg His Lys Val Pro Glu Ile Leu Glu Val Glu Val Asp Pro Lys
            340                 345                 350

Gly Gly Pro Arg Ile Gln Glu Ala Ala Met Lys Leu Tyr Val Ser Lys
            355                 360                 365

Ser Ala Phe Glu Lys Val His Leu Leu Gln Ala Met Gln Ala Ile Glu
370                 375                 380

Ala Ala Met Lys Arg Phe Phe Tyr Ala Tyr Lys Gln Val Leu Ala Val
385                 390                 395                 400

Val Met Gly Ser Ser Glu Ala Asn Gly Asn Arg Val Gly Leu Ser Cys
                405                 410                 415

Asp Ser Ala Asp Ser Leu Thr Gln Ile Phe Leu Glu Pro Thr Tyr Phe
                420                 425                 430

Pro Ser Leu Asp Ala Ala Lys Thr Phe Leu Gly Tyr Leu Trp Asp Asn
            435                 440                 445

Asn Asp Asn Asn Lys Trp Ile
450                 455
```

(2) INFORMATION FOR SEQ ID NO:7:

(i) SEQUENCE CHARACTERISTICS:
        (A) LENGTH: 1418 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Glycine max (ix) FEATURE:
        (A) NAME/KEY: CDS
        (B) LOCATION: 46..1401

(xi) SEQUENCE DESCRIPTION: SEQ ID NO:7:

```
CACCAAACAA AAAAATCAAT CATTTTATTT TATTTTTCTA CGAAA ATG GTT GAT              54
                                                Met Val Asp

TTA CAT TGG AAA TCA AAG ATG CCT AGT TCC AAA ACA CCA AAA CTC TCT          102
Leu His Trp Lys Ser Lys Met Pro Ser Ser Lys Thr Pro Lys Leu Ser
460                 465                 470                 475

CTC TCC GAC AAC AAG TCC TTA CCC TCT TTG CAA CTA CCC TTC CGC ACC          150
Leu Ser Asp Asn Lys Ser Leu Pro Ser Leu Gln Leu Pro Phe Arg Thr
                480                 485                 490

ACA GAT ATC TCT CCC GCC GCT CCT TCC GTT TGC GCC GCT TAC GAC TAC          198
Thr Asp Ile Ser Pro Ala Ala Pro Ser Val Cys Ala Ala Tyr Asp Tyr
            495                 500                 505
```

```
TAT CTC CGT CTT CCT CAA CTC AGA AAG CTT TGG AAC TCC ACT GAT TTT       246
Tyr Leu Arg Leu Pro Gln Leu Arg Lys Leu Trp Asn Ser Thr Asp Phe
        510                 515                 520

CCT AAT TGG AAC AAC GAA CCG ATT CTA AAA CCA ATT TTG CAA GCT CTC       294
Pro Asn Trp Asn Asn Glu Pro Ile Leu Lys Pro Ile Leu Gln Ala Leu
525                 530                 535

GAA ATC ACG TTC CGC TTT CTT TCC ATT GTT CTC TCC GAT CCC AGA CCT       342
Glu Ile Thr Phe Arg Phe Leu Ser Ile Val Leu Ser Asp Pro Arg Pro
540                 545                 550                 555

TAC TCC AAC CAC AGA GAA TGG ACT CGC CGG ATA GAG TCT CTC ATC ATG       390
Tyr Ser Asn His Arg Glu Trp Thr Arg Arg Ile Glu Ser Leu Ile Met
        560                 565                 570

CAT CAA ATT GAA ATC ATT GCC ATA CTT TGT GAA GAA GAG GAA CAA AAT       438
His Gln Ile Glu Ile Ile Ala Ile Leu Cys Glu Glu Glu Gln Asn
575                 580                 585

TCC GAC ACA CGT GGC ACT GCA CCA ACC GCT GAT CTC AGC AGC AGC AAT       486
Ser Asp Thr Arg Gly Thr Ala Pro Thr Ala Asp Leu Ser Ser Ser Asn
        590                 595                 600

AGC AGC GTG AGC AGA AGC TAC AGC GAG GCG AGC CTG CTT CCT CGG CTT       534
Ser Ser Val Ser Arg Ser Tyr Ser Glu Ala Ser Leu Leu Pro Arg Leu
605                 610                 615

GCC ACG TGG TAC AAA TCC AGG GAC GTG GCG CAG AGG ATC CTT CTC TCC       582
Ala Thr Trp Tyr Lys Ser Arg Asp Val Ala Gln Arg Ile Leu Leu Ser
620                 625                 630                 635

GTG GAA TGC CAA ATG AGG AGG TGC TCC TAC ACG CTT GGT TTG GGC GAG       630
Val Glu Cys Gln Met Arg Arg Cys Ser Tyr Thr Leu Gly Leu Gly Glu
        640                 645                 650

CCG AAC CTA GCG GGG AAG CCG AGC CTG CTC TAC GAC CTC GTG TGC AAG       678
Pro Asn Leu Ala Gly Lys Pro Ser Leu Leu Tyr Asp Leu Val Cys Lys
        655                 660                 665

CCG AAT GAG ATC CAC GCG CTG AAG ACG ACG CCG TAC GAC GAG CGC GTG       726
Pro Asn Glu Ile His Ala Leu Lys Thr Thr Pro Tyr Asp Glu Arg Val
        670                 675                 680

GAG AAC CAC GAG AAC CAC GCG GTG CAC GCC ACG CAC CAG ATC GCG GAG       774
Glu Asn His Glu Asn His Ala Val His Ala Thr His Gln Ile Ala Glu
685                 690                 695

TCG TGG ATT CAC GCG TCG CGG AAG GTT CTG GAG AGA ATC GCG GAC GCG       822
Ser Trp Ile His Ala Ser Arg Lys Val Leu Glu Arg Ile Ala Asp Ala
700                 705                 710                 715

GTG CTC TCC AGA ACC TTC CTG AAA GCA GCA GAG GAC TGC TAC GCC GTG       870
Val Leu Ser Arg Thr Phe Leu Lys Ala Ala Glu Asp Cys Tyr Ala Val
                720                 725                 730

GAG AGG ATC TGG AAG CTT CTC GCG GAG GTG GAG GAC CTC CAC CTG ATG       918
Glu Arg Ile Trp Lys Leu Leu Ala Glu Val Glu Asp Leu His Leu Met
            735                 740                 745

ATG GAT CCG GAC GAT TTC TTG AGG CTA AAG AAT CAA CTC TCG GTG AAA       966
Met Asp Pro Asp Asp Phe Leu Arg Leu Lys Asn Gln Leu Ser Val Lys
        750                 755                 760

TCC TCG AGC GGC GAA ACG GCA TCG TTC TGC TTC AGA TCG AAT GAG TTA      1014
Ser Ser Ser Gly Glu Thr Ala Ser Phe Cys Phe Arg Ser Asn Glu Leu
765                 770                 775

GTG GAA CTG ACG AAG ATG TGC AGA GAT CTG AGG CAC AAG GTG CCG GAG      1062
Val Glu Leu Thr Lys Met Cys Arg Asp Leu Arg His Lys Val Pro Glu
780                 785                 790                 795

ATA TTG GAG GTG GAG GTG GAT CCG AAG GGA GGA CCG AGG ATT CAA GAG      1110
Ile Leu Glu Val Glu Val Asp Pro Lys Gly Gly Pro Arg Ile Gln Glu
                800                 805                 810

GCG GCG ATG AAG CTC TAC GTT TCG AAG AGC GAG TTC GAG AAG GTT CAC      1158
Ala Ala Met Lys Leu Tyr Val Ser Lys Ser Glu Phe Glu Lys Val His
            815                 820                 825
```

```
TTG TTG CAG GCG ATG CAG GCG ATT GAG GCG GCG ATG AAG AGA TTC TTC    1206
Leu Leu Gln Ala Met Gln Ala Ile Glu Ala Ala Met Lys Arg Phe Phe
        830                 835                 840

TAC GCG TAT AAG CAG GTG TTG GCG GTG GTG ATG GGA AGT TCA GAG GCT    1254
Tyr Ala Tyr Lys Gln Val Leu Ala Val Val Met Gly Ser Ser Glu Ala
845                 850                 855

AAC GGT AAC CGA GTT GGG TTG AGT TGC GAC TCG GCT GAC TCG TTG ACT    1302
Asn Gly Asn Arg Val Gly Leu Ser Cys Asp Ser Ala Asp Ser Leu Thr
860                 865                 870                 875

CAG ATT TTC CTT GAA CCG ACG TAT TTT CCA AGC TTG GAT GCC GCC AAG    1350
Gln Ile Phe Leu Glu Pro Thr Tyr Phe Pro Ser Leu Asp Ala Ala Lys
            880                 885                 890

ACT TTT CTT GGA TAC CTG TGG GAT AAT AAC GAT AAT AAC AAA TGG ATA    1398
Thr Phe Leu Gly Tyr Leu Trp Asp Asn Asn Asp Asn Asn Lys Trp Ile
        895                 900                 905

TGA AAACGAAAAA AAAAAAA                                              1418
 *
```

(2) INFORMATION FOR SEQ ID NO:8:

(i) SEQUENCE CHARACTERISTICS:
        (A) LENGTH: 451 amino acids
        (B) TYPE: amino acid
        (D) TOPOLOGY: linear (ii) MOLECULE TYPE: protein (xi) SEQUENCE DESCRIPTION: SEQ ID NO:8:

```
Met Val Asp Leu His Trp Lys Ser Lys Met Pro Ser Ser Lys Thr Pro
 1               5                  10                  15

Lys Leu Ser Leu Ser Asp Asn Lys Ser Leu Pro Ser Leu Gln Leu Pro
             20                  25                  30

Phe Arg Thr Thr Asp Ile Ser Pro Ala Ala Pro Ser Val Cys Ala Ala
         35                  40                  45

Tyr Asp Tyr Tyr Leu Arg Leu Pro Gln Leu Arg Lys Leu Trp Asn Ser
     50                  55                  60

Thr Asp Phe Pro Asn Trp Asn Asn Glu Pro Ile Leu Lys Pro Ile Leu
 65                  70                  75                  80

Gln Ala Leu Glu Ile Thr Phe Arg Phe Leu Ser Ile Val Leu Ser Asp
                 85                  90                  95

Pro Arg Pro Tyr Ser Asn His Arg Glu Trp Thr Arg Arg Ile Glu Ser
            100                 105                 110

Leu Ile Met His Gln Ile Glu Ile Ala Ile Leu Cys Glu Glu Glu
        115                 120                 125

Glu Gln Asn Ser Asp Thr Arg Gly Thr Ala Pro Thr Ala Asp Leu Ser
    130                 135                 140

Ser Ser Asn Ser Ser Val Ser Arg Ser Tyr Ser Glu Ala Ser Leu Leu
145                 150                 155                 160

Pro Arg Leu Ala Thr Trp Tyr Lys Ser Arg Asp Val Ala Gln Arg Ile
                165                 170                 175

Leu Leu Ser Val Glu Cys Gln Met Arg Arg Cys Ser Tyr Thr Leu Gly
            180                 185                 190

Leu Gly Glu Pro Asn Leu Ala Gly Lys Pro Ser Leu Leu Tyr Asp Leu
        195                 200                 205

Val Cys Lys Pro Asn Glu Ile His Ala Leu Lys Thr Thr Pro Tyr Asp
    210                 215                 220

Glu Arg Val Glu Asn His Glu Asn His Ala Val His Ala Thr His Gln
225                 230                 235                 240
```

-continued

```
Ile Ala Glu Ser Trp Ile His Ala Ser Arg Lys Val Leu Glu Arg Ile
                245                 250                 255

Ala Asp Ala Val Leu Ser Arg Thr Phe Leu Lys Ala Ala Glu Asp Cys
            260                 265                 270

Tyr Ala Val Glu Arg Ile Trp Lys Leu Leu Ala Glu Val Glu Asp Leu
        275                 280                 285

His Leu Met Met Asp Pro Asp Asp Phe Leu Arg Leu Lys Asn Gln Leu
    290                 295                 300

Ser Val Lys Ser Ser Ser Gly Glu Thr Ala Ser Phe Cys Phe Arg Ser
305                 310                 315                 320

Asn Glu Leu Val Glu Leu Thr Lys Met Cys Arg Asp Leu Arg His Lys
                325                 330                 335

Val Pro Glu Ile Leu Glu Val Glu Val Asp Pro Lys Gly Gly Pro Arg
            340                 345                 350

Ile Gln Glu Ala Ala Met Lys Leu Tyr Val Ser Lys Ser Glu Phe Glu
        355                 360                 365

Lys Val His Leu Leu Gln Ala Met Gln Ala Ile Glu Ala Ala Met Lys
    370                 375                 380

Arg Phe Phe Tyr Ala Tyr Lys Gln Val Leu Ala Val Val Met Gly Ser
385                 390                 395                 400

Ser Glu Ala Asn Gly Asn Arg Val Gly Leu Ser Cys Asp Ser Ala Asp
                405                 410                 415

Ser Leu Thr Gln Ile Phe Leu Glu Pro Thr Tyr Phe Pro Ser Leu Asp
            420                 425                 430

Ala Ala Lys Thr Phe Leu Gly Tyr Leu Trp Asp Asn Asn Asp Asn Asn
        435                 440                 445

Lys Trp Ile
    450
```

(2) INFORMATION FOR SEQ ID NO:9:

(i) SEQUENCE CHARACTERISTICS:
        (A) LENGTH: 1498 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Glycine max (ix) FEATURE:
        (A) NAME/KEY: CDS
        (B) LOCATION: 69..1436

(xi) SEQUENCE DESCRIPTION: SEQ ID NO:9:

```
CGACACCAAT TTCTCCATCC TCTCATTGAA AAACAAAATT AATCATCTTA TTTATTTATT      60

CTCCGAAA ATG GTT GAT TTA CAT TGG AAA TCA AAG ATG CCA AGT TCC GAC     110
         Met Val Asp Leu His Trp Lys Ser Lys Met Pro Ser Ser Asp
                 455                 460                 465

ATG CCT TCC AAA ACT CTC AAA CTC TCT CTC TCC GAC AAC AAG TCC TTA     158
Met Pro Ser Lys Thr Leu Lys Leu Ser Leu Ser Asp Asn Lys Ser Leu
            470                 475                 480

CCC TCT TTG CAA CTA CCC TTC CGC ACC ACA GAT ATC TCT CAC GCC GCA     206
Pro Ser Leu Gln Leu Pro Phe Arg Thr Thr Asp Ile Ser His Ala Ala
        485                 490                 495

CCT TCT GTT TGC GCC ACT TAC GAC TAC TAT CTC CGT CTT CCT CAA CTC     254
Pro Ser Val Cys Ala Thr Tyr Asp Tyr Tyr Leu Arg Leu Pro Gln Leu
    500                 505                 510
```

```
AGA AAG CTT TGG AAC TCC TCA GAT TTT CCT AAT TGG AAC AAC GAA CCA      302
Arg Lys Leu Trp Asn Ser Ser Asp Phe Pro Asn Trp Asn Asn Glu Pro
515                 520                 525                 530

ATC TTA AAA CCT ATC TTG CAA GCT CTC GAA ATC ACC TTC CGC TTT CTC      350
Ile Leu Lys Pro Ile Leu Gln Ala Leu Glu Ile Thr Phe Arg Phe Leu
            535                 540                 545

TCC ATT GTT CTC TCC GAT CCA AGA CCT TAC TCC AAC CAC AGA GAA TGG      398
Ser Ile Val Leu Ser Asp Pro Arg Pro Tyr Ser Asn His Arg Glu Trp
        550                 555                 560

ACT CGC AGG ATA GAG TCT CTT ATC ACA CAT CAA ATT GAA ATC ATT GCC      446
Thr Arg Arg Ile Glu Ser Leu Ile Thr His Gln Ile Glu Ile Ile Ala
    565                 570                 575

ATA CTT TGT GAA GAT GAG GAA CAA AAT TCC GAC ACA CGT GGC ACT GCA      494
Ile Leu Cys Glu Asp Glu Glu Gln Asn Ser Asp Thr Arg Gly Thr Ala
580                 585                 590

CCA ACC GCT GAT CTC AGC AGG AAC AAT AGC AGC GAG AGC AGA AGC TAC      542
Pro Thr Ala Asp Leu Ser Arg Asn Asn Ser Ser Glu Ser Arg Ser Tyr
595                 600                 605                 610

AGC GAG GCA AGC CTG CTT CCG CGG CTT GCC ACG TGG TAC AAA TCC AAG      590
Ser Glu Ala Ser Leu Leu Pro Arg Leu Ala Thr Trp Tyr Lys Ser Lys
            615                 620                 625

GAC GTA GCG CAG AGG ATC CTT CTC TCA GTT GAA TGC CAA ATG AGG AGG      638
Asp Val Ala Gln Arg Ile Leu Leu Ser Val Glu Cys Gln Met Arg Arg
        630                 635                 640

TGT TCC TAC ACG CTG GGT TTG GGT GAG CCG AAC CTA GCG GGC AAA CCG      686
Cys Ser Tyr Thr Leu Gly Leu Gly Glu Pro Asn Leu Ala Gly Lys Pro
    645                 650                 655

AGC CTG CTC TAC GAC CTC GTG TGC AAG CCG AAC GAG ATC CAC GCG CTG      734
Ser Leu Leu Tyr Asp Leu Val Cys Lys Pro Asn Glu Ile His Ala Leu
660                 665                 670

AAG ACG ACG CCG TAC GAT GAG CGC GTA GAG AAT CAC GAG AAC CAC GCG      782
Lys Thr Thr Pro Tyr Asp Glu Arg Val Glu Asn His Glu Asn His Ala
675                 680                 685                 690

TTG CAC GCG ACG CAC CAG ATC GCC GAG TCG TGG ATC CAC GCG TCG CGG      830
Leu His Ala Thr His Gln Ile Ala Glu Ser Trp Ile His Ala Ser Arg
            695                 700                 705

AAG GTT CTA GAG AGG ATC GCA GAC GCG GTC CTC TCC AGA ACC TTC GAG      878
Lys Val Leu Glu Arg Ile Ala Asp Ala Val Leu Ser Arg Thr Phe Glu
        710                 715                 720

AAG GCG GCT GAG GAC TGC TAC GCC GTG GAA AGG ATC TGG AAG CTT CTC      926
Lys Ala Ala Glu Asp Cys Tyr Ala Val Glu Arg Ile Trp Lys Leu Leu
    725                 730                 735

GCG GAG GTG GAG GAC CTC CAC CTG ATG ATG GAT CCG GAC GAT TTC TTG      974
Ala Glu Val Glu Asp Leu His Leu Met Met Asp Pro Asp Asp Phe Leu
740                 745                 750

AGA CTG AAG AAT CAG CTC TCG GTG AAA TCC TCC GGC GGC GAA ACG GCT     1022
Arg Leu Lys Asn Gln Leu Ser Val Lys Ser Ser Gly Gly Glu Thr Ala
755                 760                 765                 770

TCG TTC TGC TTC AGG TCG AAG GAG TTG GTT GAA CTG ACG AAG ATG TGC     1070
Ser Phe Cys Phe Arg Ser Lys Glu Leu Val Glu Leu Thr Lys Met Cys
            775                 780                 785

AGA GAT CTG AGG CAC AAG GTG CCG GAG ATA TTG GAG GTG GAG GTG GAT     1118
Arg Asp Leu Arg His Lys Val Pro Glu Ile Leu Glu Val Glu Val Asp
        790                 795                 800

CCG AAG GGA GGA CCG AGG ATT CAA GAG GCG GCG ATG AAG CTC TAC GTT     1166
Pro Lys Gly Gly Pro Arg Ile Gln Glu Ala Ala Met Lys Leu Tyr Val
    805                 810                 815

TCG AAG AGC GCG TTC GAG AAG GTT CAC TTG TTG CAG GCG ATG CAG GCG     1214
Ser Lys Ser Ala Phe Glu Lys Val His Leu Leu Gln Ala Met Gln Ala
820                 825                 830
```

```
ATT GAG GCG GCG ATG AAG AGA TTC TTC TAC GCG TAT AAG CAG GTG TTG        1262
Ile Glu Ala Ala Met Lys Arg Phe Phe Tyr Ala Tyr Lys Gln Val Leu
835                 840                 845                 850

GCG GTG GTG ATG GGA AGC TCC GAG GCT AAC GGT AAC CGA GTT GGG TTG        1310
Ala Val Val Met Gly Ser Ser Glu Ala Asn Gly Asn Arg Val Gly Leu
                855                 860                 865

AGT TGC GAC TCG GCT GAC TCG TTG ACT CAG ATT TTC CTT GAA CCG ACG        1358
Ser Cys Asp Ser Ala Asp Ser Leu Thr Gln Ile Phe Leu Glu Pro Thr
            870                 875                 880

TAT TTT CCA AGC TTG GAT GCC GCC AAG ACT TTT CTT GGA TAC TTG TGG        1406
Tyr Phe Pro Ser Leu Asp Ala Ala Lys Thr Phe Leu Gly Tyr Leu Trp
        885                 890                 895

GAT AAT AAC GAT AAT AAC AAA TGG ATA TGA TAAGGGAAAA AAAAAAAACG          1456
Asp Asn Asn Asp Asn Asn Lys Trp Ile *
900                 905

GCACAAAAAC GATGGCCAAA GTGAGATTTT CGGTTTGGGC AC                         1498

(2) INFORMATION FOR SEQ ID NO:10:

(i) SEQUENCE CHARACTERISTICS:
        (A) LENGTH: 455 amino acids
        (B) TYPE: amino acid
        (D) TOPOLOGY: linear (ii) MOLECULE TYPE: protein (xi) SEQUENCE DESCRIPTION: SEQ ID NO:10:

Met Val Asp Leu His Trp Lys Ser Lys Met Pro Ser Ser Asp Met Pro
1               5                   10                  15

Ser Lys Thr Leu Lys Leu Ser Leu Ser Asp Asn Lys Ser Leu Pro Ser
            20                  25                  30

Leu Gln Leu Pro Phe Arg Thr Thr Asp Ile Ser His Ala Ala Pro Ser
        35                  40                  45

Val Cys Ala Thr Tyr Asp Tyr Tyr Leu Arg Leu Pro Gln Leu Arg Lys
    50                  55                  60

Leu Trp Asn Ser Ser Asp Phe Pro Asn Trp Asn Asn Glu Pro Ile Leu
65                  70                  75                  80

Lys Pro Ile Leu Gln Ala Leu Glu Ile Thr Phe Arg Phe Leu Ser Ile
                85                  90                  95

Val Leu Ser Asp Pro Arg Pro Tyr Ser Asn His Arg Glu Trp Thr Arg
            100                 105                 110

Arg Ile Glu Ser Leu Ile Thr His Gln Ile Glu Ile Ala Ile Leu
        115                 120                 125

Cys Glu Asp Glu Glu Gln Asn Ser Asp Thr Arg Gly Thr Ala Pro Thr
    130                 135                 140

Ala Asp Leu Ser Arg Asn Asn Ser Ser Glu Ser Arg Ser Tyr Ser Glu
145                 150                 155                 160

Ala Ser Leu Leu Pro Arg Leu Ala Thr Trp Tyr Lys Ser Lys Asp Val
                165                 170                 175

Ala Gln Arg Ile Leu Leu Ser Val Glu Cys Gln Met Arg Arg Cys Ser
            180                 185                 190

Tyr Thr Leu Gly Leu Gly Glu Pro Asn Leu Ala Gly Lys Pro Ser Leu
        195                 200                 205

Leu Tyr Asp Leu Val Cys Lys Pro Asn Glu Ile His Ala Leu Lys Thr
    210                 215                 220

Thr Pro Tyr Asp Glu Arg Val Glu Asn His Glu Asn His Ala Leu His
225                 230                 235                 240
```

-continued

```
Ala Thr His Gln Ile Ala Glu Ser Trp Ile His Ala Ser Arg Lys Val
            245                 250                 255

Leu Glu Arg Ile Ala Asp Ala Val Leu Ser Arg Thr Phe Glu Lys Ala
            260                 265                 270

Ala Glu Asp Cys Tyr Ala Val Glu Arg Ile Trp Lys Leu Leu Ala Glu
            275                 280                 285

Val Glu Asp Leu His Leu Met Met Asp Pro Asp Phe Leu Arg Leu
    290                 295                 300

Lys Asn Gln Leu Ser Val Lys Ser Ser Gly Gly Glu Thr Ala Ser Phe
305                 310                 315                 320

Cys Phe Arg Ser Lys Glu Leu Val Glu Leu Thr Lys Met Cys Arg Asp
            325                 330                 335

Leu Arg His Lys Val Pro Glu Ile Leu Glu Val Glu Val Asp Pro Lys
            340                 345                 350

Gly Gly Pro Arg Ile Gln Glu Ala Ala Met Lys Leu Tyr Val Ser Lys
            355                 360                 365

Ser Ala Phe Glu Lys Val His Leu Leu Gln Ala Met Gln Ala Ile Glu
            370                 375                 380

Ala Ala Met Lys Arg Phe Phe Tyr Ala Tyr Lys Gln Val Leu Ala Val
385                 390                 395                 400

Val Met Gly Ser Ser Glu Ala Asn Gly Asn Arg Val Gly Leu Ser Cys
            405                 410                 415

Asp Ser Ala Asp Ser Leu Thr Gln Ile Phe Leu Glu Pro Thr Tyr Phe
            420                 425                 430

Pro Ser Leu Asp Ala Ala Lys Thr Phe Leu Gly Tyr Leu Trp Asp Asn
            435                 440                 445

Asn Asp Asn Asn Lys Trp Ile
450                 455
```